United States Patent
Huiku

(12) 
(10) Patent No.: US 10,098,558 B2
(45) Date of Patent: Oct. 16, 2018

(54) WIRELESS PATIENT MONITORING SYSTEM AND METHOD

(71) Applicant: General Electric Company, Schenectady, NY (US)

(72) Inventor: Matti Veli Tapani Huiku, Helsinki (FI)

(73) Assignee: General Electric Company, Schenectady, NY (US)

(*) Notice: Subject to any disclaimer, the term of this patent is extended or adjusted under 35 U.S.C. 154(b) by 0 days.

(21) Appl. No.: 15/137,375

(22) Filed: Apr. 25, 2016

(65) Prior Publication Data
US 2017/0303784 A1    Oct. 26, 2017

(51) Int. Cl.
| | |
|---|---|
| A61B 5/021 | (2006.01) |
| A61B 5/0402 | (2006.01) |
| A61B 5/00 | (2006.01) |
| A61B 5/0205 | (2006.01) |
| A61B 5/1455 | (2006.01) |

(52) U.S. Cl.
CPC .......... *A61B 5/0402* (2013.01); *A61B 5/0024* (2013.01); *A61B 5/021* (2013.01); *A61B 5/02055* (2013.01); *A61B 5/721* (2013.01); *A61B 5/7475* (2013.01); *A61B 5/14551* (2013.01); *A61B 2560/0209* (2013.01); *A61B 2562/0219* (2013.01)

(58) Field of Classification Search
CPC ................................................... A61B 5/0002
USPC ..................................................... 340/870.07
See application file for complete search history.

(56) References Cited

U.S. PATENT DOCUMENTS

| | | | |
|---|---|---|---|
| 5,368,026 | A | 11/1994 | Swedlow et al. |
| 5,743,263 | A | 4/1998 | Baker, Jr. |
| 5,830,135 | A | 11/1998 | Bosque et al. |
| 6,005,658 | A | 12/1999 | Kaluza et al. |
| 6,178,343 | B1 | 1/2001 | Bindszus et al. |
| 6,594,511 | B2 | 7/2003 | Stone et al. |

(Continued)

FOREIGN PATENT DOCUMENTS

| | | |
|---|---|---|
| EP | 2470068 A2 | 7/2012 |
| EP | 2432380 A4 | 3/2013 |

(Continued)

OTHER PUBLICATIONS

Pending U.S. Appl. No. 14/586,393, filed Dec. 30, 2014, entitled Common Display Unit for a Plurality of Cableless Medical Sensors:, Muuranto et al.

*Primary Examiner* — Qutbuddin Ghulamali

(74) *Attorney, Agent, or Firm* — Andrus Intellectual Property Law, LLP

(57) ABSTRACT

A patient monitoring system includes one or more wireless sensing devices configured to record physiological data from a patient and one or more processors. An activity analysis module is executable on one or more of the processors to select an activity class from a predefined set of activity classes based on an activity input. A power management module is executable on one or more of the processors to reduce power consumption of one or more of the wireless sensing devices by identifying that one or more of the wireless sensing devices is unreliable based on the activity class, and operating the one or more unreliable wireless sensing devices in a low power mode.

21 Claims, 8 Drawing Sheets

(56) References Cited

U.S. PATENT DOCUMENTS

| | | | |
|---|---|---|---|
| 7,111,179 B1* | 9/2006 | Girson | G06F 1/3203 320/130 |
| 7,803,120 B2 | 9/2010 | Banet et al. | |
| 7,993,275 B2 | 8/2011 | Banet et al. | |
| 8,180,440 B2 | 5/2012 | McCombie et al. | |
| 8,200,321 B2 | 6/2012 | McCombie et al. | |
| 8,239,010 B2 | 8/2012 | Banet et al. | |
| 8,321,004 B2 | 11/2012 | Moon et al. | |
| 8,359,080 B2 | 1/2013 | Diab et al. | |
| 8,364,226 B2 | 1/2013 | Diab et al. | |
| 8,364,250 B2 | 1/2013 | Moon et al. | |
| 8,419,649 B2 | 4/2013 | Banet et al. | |
| 8,437,824 B2 | 5/2013 | Moon et al. | |
| 8,442,607 B2 | 5/2013 | Banet et al. | |
| 8,449,469 B2 | 5/2013 | Banet et al. | |
| 8,475,370 B2 | 7/2013 | McCombie et al. | |
| 8,506,480 B2 | 8/2013 | Banet et al. | |
| 8,527,038 B2 | 9/2013 | Moon et al. | |
| 8,545,417 B2 | 10/2013 | Banet et al. | |
| 8,554,297 B2 | 10/2013 | Moon et al. | |
| 8,570,167 B2 | 10/2013 | Al-Ali | |
| 8,571,893 B2 | 10/2013 | Dashefsky et al. | |
| 8,574,161 B2 | 11/2013 | Banet et al. | |
| 8,591,411 B2 | 11/2013 | Banet et al. | |
| 8,594,776 B2 | 11/2013 | McCombie et al. | |
| 8,602,997 B2 | 12/2013 | Banet et al. | |
| 8,622,922 B2 | 1/2014 | Banet et al. | |
| 8,672,854 B2 | 3/2014 | McCombie et al. | |
| 8,721,542 B2 | 5/2014 | Al-Ali et al. | |
| 8,727,977 B2 | 5/2014 | Banet et al. | |
| 8,738,118 B2 | 5/2014 | Moon et al. | |
| 8,740,802 B2 | 6/2014 | Banet et al. | |
| 8,740,807 B2 | 6/2014 | Banet et al. | |
| 8,747,330 B2 | 6/2014 | Banet et al. | |
| 8,808,188 B2 | 8/2014 | Banet et al. | |
| 8,847,740 B2 | 9/2014 | Kiani et al. | |
| 8,852,094 B2 | 10/2014 | Al-Ali et al. | |
| 8,888,700 B2 | 11/2014 | Banet et al. | |
| 8,909,330 B2 | 12/2014 | McCombie et al. | |
| 8,956,293 B2 | 2/2015 | McCombie et al. | |
| 8,956,294 B2 | 2/2015 | McCombie et al. | |
| 8,979,765 B2 | 3/2015 | Banet et al. | |
| 8,989,853 B2 | 3/2015 | Zong | |
| 9,055,928 B2 | 6/2015 | McCombie et al. | |
| 9,095,316 B2 | 8/2015 | Welch et al. | |
| 9,149,192 B2 | 10/2015 | Banet et al. | |
| 9,161,700 B2 | 10/2015 | Banet et al. | |
| 9,173,593 B2 | 11/2015 | Banet et al. | |
| 9,173,594 B2 | 11/2015 | Banet et al. | |
| 9,215,986 B2 | 12/2015 | Banet et al. | |
| 2005/0101873 A1 | 5/2005 | Misczynski et al. | |
| 2007/0167850 A1 | 7/2007 | Russell et al. | |
| 2008/0300471 A1 | 12/2008 | Al-Ali et al. | |
| 2009/0171167 A1 | 7/2009 | Baker, Jr. | |
| 2009/0275807 A1 | 11/2009 | Sitzman et al. | |
| 2010/0063367 A1 | 3/2010 | Friedman et al. | |
| 2010/0160794 A1 | 6/2010 | Banet et al. | |
| 2010/0160795 A1 | 6/2010 | Banet et al. | |
| 2010/0160796 A1 | 6/2010 | Banet et al. | |
| 2010/0160797 A1 | 6/2010 | Banet et al. | |
| 2010/0160798 A1 | 6/2010 | Banet et al. | |
| 2010/0168589 A1 | 7/2010 | Banet et al. | |
| 2011/0080294 A1 | 4/2011 | Tanishima et al. | |
| 2011/0224498 A1 | 9/2011 | Banet et al. | |
| 2011/0224499 A1 | 9/2011 | Banet et al. | |
| 2011/0224500 A1 | 9/2011 | Banet et al. | |
| 2011/0224506 A1 | 9/2011 | Moon et al. | |
| 2011/0224507 A1 | 9/2011 | Banet et al. | |
| 2011/0224508 A1 | 9/2011 | Moon | |
| 2011/0224556 A1 | 9/2011 | Moon et al. | |
| 2011/0224557 A1 | 9/2011 | Banet et al. | |
| 2011/0224564 A1 | 9/2011 | Moon et al. | |
| 2011/0257489 A1 | 10/2011 | Banet et al. | |
| 2011/0257551 A1 | 10/2011 | Banet et al. | |
| 2011/0257552 A1 | 10/2011 | Banet et al. | |
| 2011/0257553 A1 | 10/2011 | Banet et al. | |
| 2011/0257554 A1 | 10/2011 | Banet et al. | |
| 2011/0257555 A1 | 10/2011 | Banet et al. | |
| 2011/0288421 A1 | 11/2011 | Banet et al. | |
| 2012/0029300 A1 | 2/2012 | Paquet | |
| 2012/0108983 A1 | 5/2012 | Banet et al. | |
| 2012/0190949 A1 | 7/2012 | McCombie et al. | |
| 2013/0109937 A1 | 5/2013 | Banet et al. | |
| 2013/0116515 A1 | 5/2013 | Banet et al. | |
| 2014/0025010 A1 | 1/2014 | Stroup et al. | |
| 2014/0081099 A1 | 3/2014 | Banet et al. | |
| 2014/0088385 A1 | 3/2014 | Moon et al. | |
| 2014/0142445 A1 | 5/2014 | Banet et al. | |
| 2014/0142459 A1* | 5/2014 | Jayalth | A61B 5/0022 600/547 |
| 2014/0163393 A1 | 6/2014 | McCombie et al. | |
| 2014/0200415 A1 | 7/2014 | McCombie et al. | |
| 2014/0235964 A1 | 8/2014 | Banet et al. | |
| 2014/0257056 A1 | 9/2014 | Moon et al. | |
| 2014/0275818 A1 | 9/2014 | Kassem et al. | |
| 2014/0276145 A1 | 9/2014 | Banet et al. | |
| 2014/0276175 A1 | 9/2014 | Banet et al. | |
| 2014/0301893 A1 | 10/2014 | Stroup et al. | |
| 2015/0042466 A1 | 2/2015 | Kiani et al. | |
| 2015/0164437 A1 | 6/2015 | McCombie et al. | |
| 2015/0196257 A1 | 7/2015 | Yousefi et al. | |
| 2015/0208966 A1 | 7/2015 | Al-Ali | |
| 2015/0282717 A1 | 10/2015 | McCombie et al. | |

FOREIGN PATENT DOCUMENTS

| | | |
|---|---|---|
| EP | 2162059 A4 | 10/2013 |
| EP | 2470067 A4 | 10/2013 |
| EP | 2560550 A4 | 12/2013 |
| EP | 2675346 A1 | 12/2013 |
| EP | 2675348 A1 | 12/2013 |
| EP | 2775917 A2 | 9/2014 |
| EP | 2432378 A4 | 12/2014 |
| EP | 24442709 A4 | 12/2014 |
| EP | 2519144 A4 | 3/2015 |
| EP | 2658440 A4 | 4/2015 |
| EP | 2544584 A4 | 7/2015 |
| EP | 2910182 A2 | 8/2015 |
| WO | 2008154643 A1 | 12/2008 |
| WO | 2010135516 A2 | 11/2010 |
| WO | 2010148205 A1 | 12/2010 |
| WO | 2011032132 A2 | 3/2011 |
| WO | 2011032132 A3 | 3/2011 |
| WO | 2011034881 A1 | 3/2011 |
| WO | 2011082341 A1 | 7/2011 |
| WO | 2011112782 A1 | 9/2011 |
| WO | 2011133582 A1 | 10/2011 |
| WO | 2010135518 A1 | 11/2011 |
| WO | 2012077113 A2 | 6/2012 |
| WO | 2012092303 A1 | 7/2012 |
| WO | 2012112885 A1 | 8/2012 |
| WO | 2012112891 A1 | 8/2012 |
| WO | 2013071014 A2 | 5/2013 |
| WO | 2013071014 A3 | 5/2013 |
| WO | 2014015254 A1 | 1/2014 |
| WO | 2014165620 A1 | 10/2014 |
| WO | 2015120330 A1 | 8/2015 |
| WO | 2015173539 A1 | 11/2015 |

* cited by examiner

| | 3a ECG/HR | 3a ECG/ECG Rhythm | 3c SpO2/SpO2 | 3c SpO2/PR | 3b NIBP |
|---|---|---|---|---|---|
| 64 Standard mode | 62 Lying, Reclining | Lying, Reclining | Lying, Reclining, Sitting, Standing | Lying, Reclining, Sitting, Standing | Lying, Reclining |
| 66a Low power mode A | 62 Sitting, Standing | Sitting | | 62 Walking | Sitting |
| 66b Low power mode B | Moving | Standing, Moving | Walking, Moving, Moving hands/fingers | Moving, Moving hands/fingers | Standing, Moving |

FIG. 5

WIRELESS PATIENT MONITORING SYSTEM AND METHOD

BACKGROUND

The present disclosure relates generally to medical devices and, more specifically, to medical monitoring devices for monitoring a patient's physiology and health status.

In the field of medicine, physicians often desire to monitor multiple physiological characteristics of their patients. Oftentimes, patient monitoring involves the use of several separate monitoring devices simultaneously, such as a pulse oximeter, a blood pressure monitor, a heart monitor, a temperature monitor, etc. Several separate patient monitoring devices are often connected to a patient, tethering the patient to multiple bulky bedside devices via physical wiring or cables. Multi-parameter monitors are also available where different sensor sets may be connected to a single monitor. However, such multi-parameter systems may be even more restrictive than separate monitoring devices because they require all of the sensors attached to a patient to be physically attached to a single monitor, resulting in multiple wires running across the patient's body. Thus, currently available patient monitoring devices often inhibit patient movement, requiring a patient to stay in one location or to transport a large monitor with them when they move from one place to another.

Further, currently available monitoring devices are often power intensive and either require being plugged in to a wall outlet or require large battery units that have to be replaced and recharged every few hours. Thus, monitoring multiple patient parameters is power intensive and battery replacement is costly in labor and parts. Thus, frequent monitoring is often avoided in order to limit cost and patient discomfort, and instead patient parameters are infrequently spot checked, such as by periodic nurse visits one or a few times a day. While there are some patients that require continuous, real-time monitoring, such as those patients experiencing a critical health condition, the vast majority of patients need only periodic monitoring to check that their condition has not changed. However, patients that are not being regularly monitored may encounter risky health situations that go undetected for a period of time, such as where rapid changes occur in physiological parameters that are not checked by a clinician until hours later or until a critical situation occurs.

SUMMARY

This Summary is provided to introduce a selection of concepts that are further described below in the Detailed Description. This Summary is not intended to identify key or essential features of the claimed subject matter, nor is it intended to be used as an aid in limiting the scope of the claimed subject matter.

One embodiment of a patient monitoring system includes one or more wireless sensing devices configured to record physiological data from a patient and one or more processors. An activity analysis module is executable on one or more of the processors to select an activity class from a predefined set of activity classes based on an activity input. A power management module is executable on one or more of the processors to reduce power consumption of one or more of the wireless sensing devices by identifying that one or more of the wireless sensing devices is unreliable based on the activity class and operating the one or more unreliable wireless sensing devices in a low power mode.

One embodiment of a method of monitoring a patient includes recording physiological data from the patient with each of at least two wireless sensing devices, wherein each wireless sensing device measures a different type of physiological data, and receiving an activity input at a processor. The method further includes selecting with the processor an activity class based on an activity input, identifying at least one wireless sensing device that is unreliable based on the activity class, and operating the one or more unreliable wireless sensing devices in a low power mode.

BRIEF DESCRIPTION OF THE DRAWINGS

The present disclosure is described with reference to the following Figures.

FIG. 5 depicts one embodiment of operation modes and a predefined set of activity classes.

DETAILED DESCRIPTION

Figure 1:
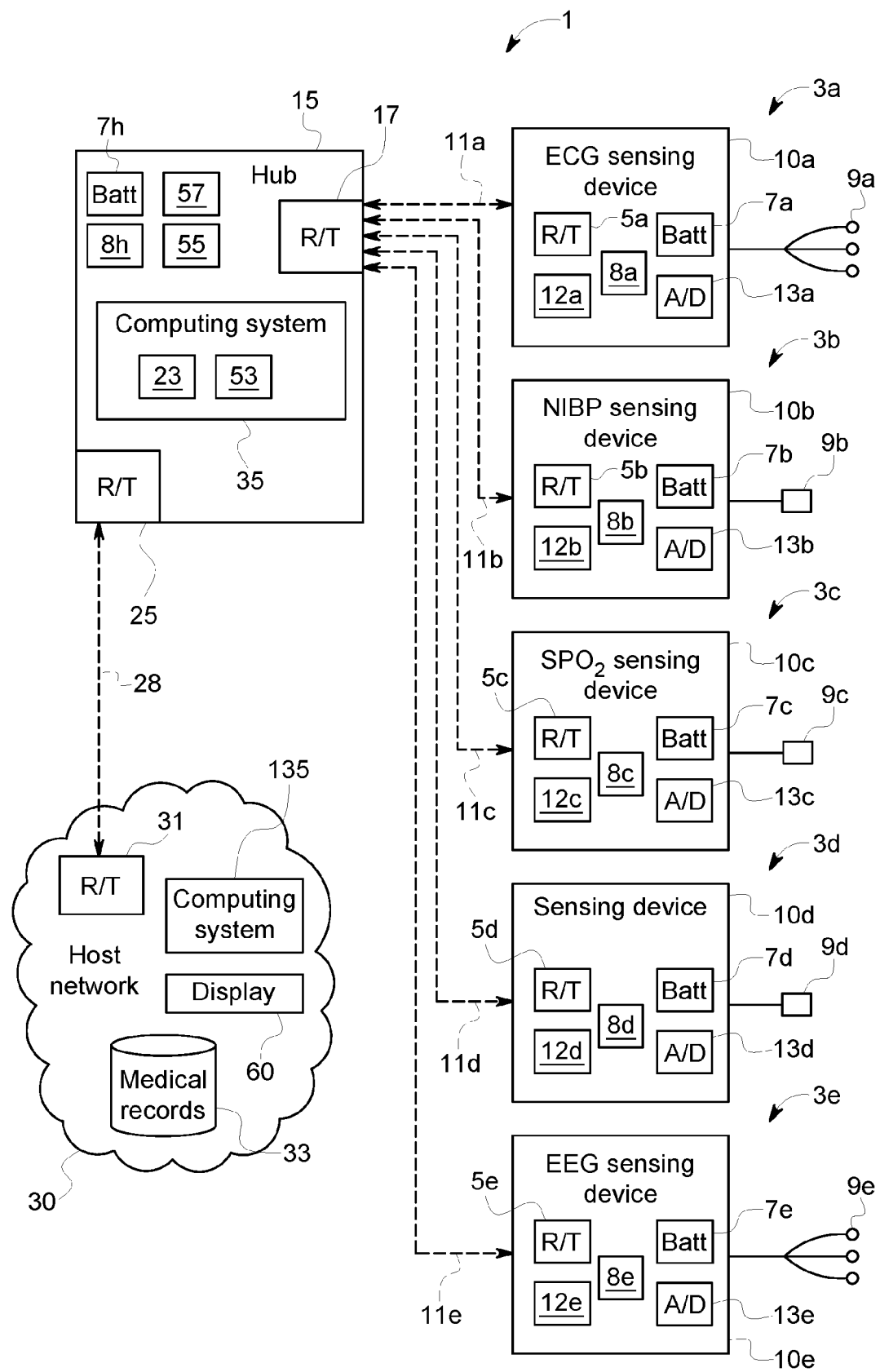
FIG. 1 is a schematic diagram of one embodiment of a wireless patient monitoring system.

The present inventor has recognized that wireless monitoring systems are desirable for patient comfort, for example to provide more comfort and mobility to the patient being monitored. The patient's movement is not inhibited by wires between sensor devices and/or computing devices that collect and process the physiological data from the patient. Thus, small sensing devices and sensors that can be easily attached to the patient's body are desirable, such as sensing devices that are wearable portable computing devices. In order to do so, the size of the wireless sensing devices must be small. The present inventor has recognized that an important aspect of decreasing the size and weight of wireless sensing devices is decreasing battery size, and that a weakness in the development of wireless sensing devices has been power consumption and requirement for long battery times.

In view of his recognition of problems and challenges in the development of wireless sensing devices, the present inventor developed the disclosed system and method to minimize power consumption of the wireless sensing devices. As provided herein, battery demand for each wireless sensing device and a hub device, and thus power requirements for the system as a whole, are decreased by selectively and intelligently operating the wireless sensing devices at times when valid data is most likely to be obtained. In other words, the system avoids wasting battery life by avoiding recording, transmitting, and/or processing physiological data that is unreliable due to artifact, patient position, etc.

In the patient monitoring system 1 and method 80 disclosed herein, one or more wireless sensing devices (e.g., 3a-3e) are controlled individually to operate in a low power mode when a patient's activity is not conducive for recording reliable physiological data. A wireless sensing device within the patient monitoring system 1 may be deemed unreliable where significant artifact is likely to be present in the physiological signals caused by the patient's activity or motion, or because the patient is in an inappropriate position or orientation for recording the relevant physiological data.

The low power mode operation may be different for each type of wireless sensing device (e.g., 3a-3e) in the system 1 depending on the type of physiological monitoring performed by that device and the medical needs of the patient. For example, when a patient's activity level, which may be classified into an activity class, indicates that the physiological data recorded from a particular wireless sensing device will be, or is likely to be, unreliable due to patient position or artifact caused by motion of the patient, one or more of the wireless sensing devices 3a-3e may be operated in a low power mode to turn off the recording and data processing functions of the device. Alternatively or additionally, certain wireless sensing devices 3a-3e in the system 1 may be operated in a low power mode to record a reduced set of physiological data from the patient, or to record the respective physiological data from the patient less frequently than when the device is in its standard operating mode. Moreover, the low power mode operation may be configured to account for health information specific to the patient, such as a diagnosis or a medical history for the patient (e.g., recent medical procedures performed, medication being administered, or the like).

Accordingly, the wireless sensing devices 3a-3e are intelligently controlled to enable any monitoring appropriate for a patient, including continuous monitoring capabilities when necessary, but can be operated in a low power mode when the patient is moving or in the presence of artifact or adverse monitoring conditions in order to reduce the power requirements of the wireless sensing devices and increase the battery life of the devices in the system.

In various embodiments, an activity class may be selected from a predefined set of activity classes based on an activity input. The activity inputs may be input from a motion sensor and/or a position sensor, for example, somehow attached to the patient. Alternatively or additionally, the activity input may be provided by the physiological data recorded by the sensing device, such as artifact or other morphological feature in the recorded physiological data. In still other embodiments, the activity input may be a user-provided input, such as where a patient or caretaker can select an activity mode when the monitored patient engages in particular activities, such as sitting, standing, walking, rolling over, etc.

In various embodiments, wireless sensing devices (e.g., 3a-3e) measuring different physiological parameters may be networked to a central hub device (e.g., 15) or primary sensing device that determines the activity class and instructs each wireless sensing device in the network to operate in an appropriate operation mode based on the activity class. The hub may communicate with a central, host network (e.g., 30), such as of the medical facility. In another embodiment, the wireless sensing devices may communicate with the host network, which may determine the activity class and assign the operation modes. There, the wireless sensing devices may communicate with the host network directly, or indirectly through the hub. For instance, the hub may serve as an amplifier and/or router for communication between the wireless sensing devices and the host network. In still other embodiments, one or more of the wireless sensing devices may determine its own local activity class based on activity input received at the wireless sensing device. In such an embodiment, the wireless sensing device may transmit the local activity class and/or the local activity input to the hub module and/or host network, which may then determine an activity class for the system, which may be utilized to control the operation mode of one or more of the other sensing devices within the system. These and other embodiments are described in more detail with respect to the Figures.

FIG. 1 depicts one embodiment of a patient monitoring system 1 containing five wireless sensing devices 3a-3e in wireless communication with a hub device 15. The hub device 15 is in wireless communication with a host network 30 that contains medical records database 33 and a computing system 135 that may operate a central monitoring function for a healthcare facility or a portion thereof. Further, the computing system 135 and/or the host network 30 may provide one or more central monitoring stations having user interfaces at central locations for attending clinicians to monitor patient conditions and/or receive alarm notifications. For example, the computing system 135 may operate at least one display 60, such as a central patient monitoring display associated with the central monitoring system, such as for a unit or section of a healthcare facility.

The hub device 15 may be attached to the patient's body, placed on or near the patient's bed, or positioned within range of the patient, such as in the same room as the patient. The hub device 15 may be a separate, stand-alone device, or it may be incorporated and/or housed with another device within the system 1, such as housed with one of the wireless sensing devices 3a-3e. For example, the hub device 15 may be a patient monitor, as the term will be understood by a person having ordinary skill in the relevant art, or it may be a separate device that communicates with a patient monitor, wherein the patient monitor then communicates with host network 30.

Each wireless sensing device 3a-3e contains one or more sensors 9a-9e for measuring a physiological parameter from a patient, and also includes a base unit 10a-10e that receives the physiological parameter measurements from the sensors 9a-9e and transmits physiological data based on those measurements to the hub device 15 via communication link 11a-11e. The sensors 9a-9e may be connected to the respective base unit 10a-10e by wired or wireless means. The sensors 9a-9e may be any sensors, leads, or other devices available in the art for sensing or detecting physiological information from a patient, which may include but are not limited to electrodes, lead wires, or available physiological measurement devices such as pressure sensors, flow sensors, temperature sensors, blood pressure cuffs, pulse oximetry sensors, voltage sensors, or the like.

In the depicted embodiment, a first wireless sensing device 3a is an ECG sensing device having sensors 9a that are ECG electrodes. A second wireless sensing device 3b is a non-invasive blood pressure (NIBP) sensing device with a sensor 9b that is a blood pressure cuff including pressure sensors. A third wireless sensing device 3c is a peripheral oxygen saturation (SpO2) monitor having sensor 9c that is a pulse oximetry sensor, such as a pulse oximetry sensor incorporating a red LED and an infrared LED configured for placement on a patient's fingertip. A fourth wireless sensing device 3d is a temperature monitor having sensor 9d that is a temperature sensor. The depicted embodiment of the system 1 further includes a fifth wireless sensing device 3e that is an EEG monitor having sensors 9e that are EEG electrodes. It should be understood that the patient monitoring system 1 of the present disclosure is not limited to the examples of sensor devices provided, but may be configured and employed to sense and monitor any clinical parameter. For example, the patient monitoring system may further include a wireless respiration rate sensing device, such as a pneumograph or a capnograph. The examples of wireless sensing devices provided herein are for the purposes of demonstrating the invention and should not be considered limiting, as any wireless device for sensing and/or recording physiological data may be incorporated within the system 1.

The base units 10a-10e of each of the exemplary wireless sensing devices 3a-3e may include analog-to-digital (A/D) converters 13a-13e, which may be any devices or logic sets capable of digitizing analog physiological signals recorded by the associated sensors 9a-9e. For example, the A/D converters 13a-13e may be Analog Front End (AFE) devices. The base units 10a-10e may further include processors 12a-12e that receive the digital physiological data from the A/D converters 13a-13e and create a parameter dataset for transmission to the hub device 15 and/or the host network 30. Each base unit 10a-10e may be configured differently depending on the type of wireless sensing device, and may be configured to perform various signal processing functions and or sensor control functions. To provide just a few examples, the processor 12a in the ECG sensing device 3a may be configured to filter the digital signal from the ECG sensors 9a to remove artifact and/or to perform various calculations and determinations based on the recorded cardiac data, such as heart rate, QRS interval, ST-T interval, or the like. The processor 12b in the NIBP monitor 3b may be configured, for example, to process the physiological data recorded by the sensors 9b in a blood pressure cuff to calculate systolic, diastolic, and mean blood pressure values for the patient. The processor 12c of the SpO2 sensing device 3c may be configured to determine a blood oxygenation value and/or a pulse rate for the patient based on the digitized signal received from the pulse oximetry sensor 9c. The processor 12d of the temperature sensing device 3d may be configured to, for example, determine a temperature for the patient, such as a mean temperature based on the digitized temperature data received from the thermal sensor 9d. And the processor 12e of the EEG sensing device 3e may be configured, for example, to determine a depth of anesthesia measurement value, such as an entropy value or a sedation responsiveness index value.

Accordingly, the processor 12a-12e may develop a dataset that, in addition to the recorded physiological data, also includes values measured and/or calculated from the recorded physiological data. The respective processor 12a-12e may then control a receiver/transmitter 5a-5e in the relevant wireless sensing device 3a-3e to transmit parameter datasets to the hub device 15 via communication link 11a-11e. The parameter dataset transmitted from the respective wireless sensing device 3a-3e may include the raw digitized physiological data, filtered digitized physiological data, and/or processed data (e.g., alarm status or alarm data) indicating information about the respective physiological parameter measured from the patient.

In other embodiments, the processors 12a-12e may not perform any signal processing tasks and may simply be configured to perform necessary control functions for the respective wireless sensing device 3a-3e. In such an embodiment, the parameter data set transmitted by the respective processor 12a-12e may simply be the digitized raw data or digitized filtered data from the various sensor devices 9a-9e.

One or more of the wireless sensing devices 3a-3e may include an activity sensor 8a-8e. Alternatively or additionally, the hub device 15 may contain activity sensor 8h. The activity sensor(s) 8a-8e, 8h are orientation and/or motion sensors that provide information about the patient's position and/or movement. For example, each activity sensor 8a-8e, 8h may be or include an accelerometer, such as a three-axis accelerometer, to measure motion information that may be used to determine a patient's activity or activity level. Alternatively or additionally, each activity sensor 8a-8e and 8h may be or include a gyroscope, such as a three-axis gyroscope, to detect orientation information that may be used to determine the position of a patient's body or body part. In still other embodiments, the activity sensor 8a-8e, 8h may be another type of inertial sensor, such as a combination accelerometer and/or gyroscope with a magnetometer.

The activity input 41a-41e, 41h (FIG. 3 and FIG. 4), which may be provided in whole or in part by the activity sensors 8a-8e, 8h, is used to determine an activity class 49, which then dictates the operation mode 64, 66a, 66b for each wireless sensing device 3a-3e. For example, the operation mode 64 may include a standard operating mode 64 and one or more low power modes 66a, 66b that conserve energy by avoiding recording, transmitting, and/or processing unreliable physiological data. As provided in more detail herein, the activity class 49 may be determined by a processor 12a-12e, 19, 119 executing an activity analysis module 23 software instruction set. The operation mode 64, 66a, 66b may be determined by a power management module 53 software instruction set.

Each activity sensor 8a-8e and 8h supplies data received as activity input 41a-41e, 41h into the system 1. The respective activity input 41a-41e, 41h is analyzed to determine an activity class 49, which may be selected from a predefined set of activity classes 62. FIG. 5 depicts an exemplary predefined set of activity classes 62 and how those classes may be used by the system 1 to determine an operation mode 64, 66a, 66b. For example, the activity input 41a-41e, 41h may be classified into one of the exemplary listed predefined set of activity classes 62, which include lying, reclining, sitting, standing, moving, walking, and moving hands/fingers (all comprising the predefined of activity classes 62). These classes are for exemplary purposes and it should be understood that different classes defining any number of positions and/or activities or motions may be used effectively.

In the chart shown at FIG. 5, each of the activity classes in the predefined set of activity classes 62 is classified into an operation mode for several listed wireless sensing devices 3a-3c and operations thereof, including an ECG sensing device 3a operating to determine a heart rate, the ECG sensing device 3a operating to record a full ECG rhythm, an SpO2 sensing device 3c operating to measure SpO2, the SpO2 sensing device 3c operating to measure a pulse rate, and an NIBP sensing device 3b. Three operating modes 64, 66a, 66b are represented a column below each listed device 3a-3c and recording function. The top cell represents the standard operating mode 64, wherein the respective wireless sensing device 3a-3c is operated in whatever operating mode is most appropriate to monitor the patient, such as based on the patient's health condition. The standard operating mode 64 is implemented when the conditions are most appropriate for reliably recording the respective physiological data. Thus, the classes listed in the top cell of each column represent those classes from predefined set of activity classes 62 in which the standard operating mode 64 may be utilized or instructed for the respective wireless sensing device 3a-3c to record the respective physiological data.

The classes listed in the middle and bottom cells are those classes from the predefined set of activity classes 62 where a low power mode 66 is implemented. In the depicted embodiment, there are two low power modes 66—low power mode A 66a and low power mode B 66b. As an example, low power mode A 66a may be obtaining the physiological data intermittently, or less frequently than would be obtained in the standard operating mode 64a. Alternatively, the low power mode A 66a may be operating with a more limited lead set or sensing operation. For example, the ECG sensing device 3a may be operated in low power mode A 66a with a reduced lead set, such as with 6, 3, 2, or 1 leads, compared to its standard operation mode 64. Likewise, the SpO2 device 3c may be operated in low power mode A 66a to take measurements less frequently than in the standard operation mode 64, or to only utilize one LED and to restrict the measurement operation to only measure pulse rate. In some embodiments, the NIBP sensing device 3b may also be operated in a low power mode A 66a, such as by measuring blood pressure less frequently or by using an abbreviated blood pressure determination or estimation algorithm that requires less cuff inflation time.

The bottom cell of each column represents the activity classes from the predefined set of activity classes 62 for which the respective wireless sensing devices 3a-3c will be operated in low power mode B 66b for recording the respective physiological data. The wireless sensing devices 3a-3c operating in low power mode B 66b consume even less power than in low power mode A 66a. For example, low power mode B 66b may be a cessation of all recording and data processing functions of the respective wireless sensing device 3a-3c. In another embodiment, the low power mode B 66b may be operating the respective wireless sensing device 3a-3c at a minimum measurement interval, which may be a predefined and stored value representing the lowest interval at which the respective physiological parameter should be measured for the particular patient. For example, a minimum measurement interval may be set for each wireless sensing device 3a-3e, which may be based on patient care standards, patient diagnosis, patient medical history, and/or previous monitoring data for the patient, and the device operating in low power mode may operate to measure the patient data at that minimum interval.

Accordingly, in the depicted embodiment, if the patient is lying or reclining, then all wireless patient monitors 3a-3c and monitoring functions may be operated in the standard operating mode 64. By contrast, if the activity input 41 indicates that the patient activity class 49 is "moving", then all wireless patient monitors 3a-3c are operated in the low power mode B 66b with respect to all physiological parameters. In certain predefined set of activity classes 62, the wireless sensing devices 3a-3c may be operated differently from one another. This concept is exemplified in FIG. 5. In the example, if the patient activity class 49 is "sitting", then the ECG sensing device 3a will be operated in the low power mode A 66a to record the heart rate and the ECG rhythm, the NIBP sensing device 3b will be operated in low power mode A 66a, and the SpO2 sensing device 3c will be operated in the standard operating mode 64 to record the SpO2 and the pulse rate. If the patient activity class 49 is "standing", then the ECG sensing device 3a will be operated in the low power mode A 66a to measure the heart rate and in low power mode B 66b to record the ECG rhythm, the NIBP sensing device 3b will be operated in low power mode B 66b (such as by being turned off because blood pressure measurements taken in the standing position are not meaningful) and the SpO2 sensing device 3c will be operated in the standard operating mode 64. In certain embodiments, these patient activity class 49 settings may be modified if local activity is detected by a local activity sensor 8a-8e, 8h or artifact is detected in the physiological data.

In various embodiments, only certain of the wireless sensing devices 3a-3e may contain an activity sensor 8a-8e. For example, it may be desirable to include an activity sensor 8a-8e in those wireless sensing devices 3a-3e that operate most frequently to monitor a patient and/or those wireless sensing devices 3a-3e that are most sensitive to artifact interference, thereby providing the opportunity to conserve the battery 7a-7e of the respective sensing device and/or the battery 7h of hub device 15 by offering particularized activity input 41a-41e relevant to motion occurring locally at that wireless sensing device 3a-3e. To provide just one example, it may be desirable to include activity sensor 8c in the SpO2 sensing device 3c, which may be operated continuously to monitor SpO2 and/or pulse rate of the patient and is relatively sensitive to monitoring data corruption due to artifact caused by patient movement. For instance, if the patient is moving only their hand, and no other part of their body, the SpO2 data may be unreliable and thus the battery life of the SpO2 sensing device 3c would be wasted by trying to obtain the SpO2 data during the motion. However, a system 1 having only an activity sensor 8h in the hub device 15 likely would not detect isolated motion in the patient's hand unless the hub device 15 was attached to the patient's hand or arm. In a system 1 having SpO2 sensing device 3c with an activity sensor 8c, the SpO2 sensing device 3c may be placed in a low power mode upon detection of hand activity, where sensing operation may be suspended when the activity input 41c supplied by the activity sensor 8c indicates that the patient's hand is in motion. A separate activity class of the predefined activity classes 62 may be provided for such activity, which is depicted as the "moving hands/fingers" predefined activity class 62 in FIG. 5. To conserve battery life, the SpO2 measurement by the SpO2 sensing device 3c may be suspended until the activity input 41c from the activity sensor 8c indicates that the motion has subsided sufficiently such that the SpO2 data can be reliably measured and will be without significant motion artifact. Alternatively, the SpO2 sensing device 3c may operate in a limited capacity in low power mode A 66a, as explained above.

The activity input 41c collected by the activity sensor 8c of the SpO2 sensing device 3c may be transmitted via communication link 11c to the hub device 15 and/or to the host network 30. The same is true for activity input 41a-41e collected by any other activity sensor 8a-8e in a wireless sensing device 3a-3e. In one embodiment, the hub device 15 may also include an activity sensor 8h, such as in an embodiment where the hub device 15 is worn on or affixed to the patient's body (such as strapped or adhered to the patient's chest). Again, the activity sensor 8h may be in addition to or in place of the activity sensors 8a-8e which may be provided locally in one or more of the wireless sensing devices 3a-3e. Thus, in certain embodiments, the activity input 41 to the system may be provided by just one activity sensor, which may be any of the activity sensors 8a-8e or 8h, or it may be provided by a subset of sensors 8a-8e, 8h or all of those sensors.

In another embodiment, the activity input 41 may include the detection of artifact or certain unwanted waveform features in the physiological data measured by the sensors 9a-9e. For example, a large amount of noise detected in the physiological signal may be used as activity input 41a-41e indicating that the patient is moving. Such type of activity input 41a-41e from the physiological signals may be in place of or in addition to input from an activity sensor 8a-8e, 8h. For example, the system 1 may include a hub device 15 with an activity sensor 8h that supplies activity input 41h, and then may obtain activity input 41a-41e at the location of certain of the wireless sensing devices 3a-3e based on the recorded physiological signal, such as by analysis of the signal to noise ratio or other artifact detection algorithms. In still other embodiments, the activity input 41 may include user-provided input, such as inputs through a user-interface 40 of the hub device 15. For example, the hub device 15 may include a mode input button 57 that may allow a user to select an activity class 49 from the predefined set of activity classes 62. For example, if the patient is going to go walking, they may select a "walking" activity class 49 via user input button 57 or other user interface means.

Each wireless sensing device 3a-3e includes a battery 7a-7e that stores energy and powers the various aspects of the wireless monitor. Each processor 12a-12e may further include power management capabilities, especially where the respective wireless sensing device 3a-3e contains more demanding electromechanical aspects. Each processor 12a-12e may monitor a battery status, such as a charge level of the relevant battery 7a-7e. The processor 12a-12e may communicate the battery status to the hub device 15 by the communication link 11a-11e. Alternatively or additionally, the processor 12a-12e may control a local display on the wireless sensing device 3a-3e to display the battery status, and/or may control the emission of an audio and/or visual alert regarding the battery status. Further, the hub device 15 may identify one or more wireless sensing devices 3a-3e with the lowest battery charge and may favor operating those devices in the low power mode 66a, 66b, if possible based on the activity class 49 and/or activity input 41a-41e, 41h. Thereby, the power usage of the system can be balanced and the system as a whole can reach longer operation time on one batter charge cycle.

The receiver/transmitter 5a-5e of each wireless sensing device 3a-3e communicates via the respective communication link 11a-11e with the receiver/transmitter 17 of the hub device 15, which may include separate receiving and transmitting devices or may include an integrated device providing both functions, such as a transceiver. The receiver/transmitters 5a-5e of the wireless sensing devices 3a-3e and the receiver/transmitter 17 of the hub device 15 may be any radio frequency devices known in the art for wirelessly transmitting data between two points. In one embodiment, the receiver/transmitters 5a-5e and 17 may be body area network (BAN) devices, such as medical body area network (MBAN) devices, that operate as a wireless network. For example, the wireless sensing devices 3a-3e may be wearable or portable computing devices in communication with a hub device 15 positioned in proximity of the patient. Other examples of radio protocols that could be used for this purpose include, but are not limited to, Bluetooth, Bluetooth Low Energy (BLE), ANT, and ZigBee.

Figure 3:
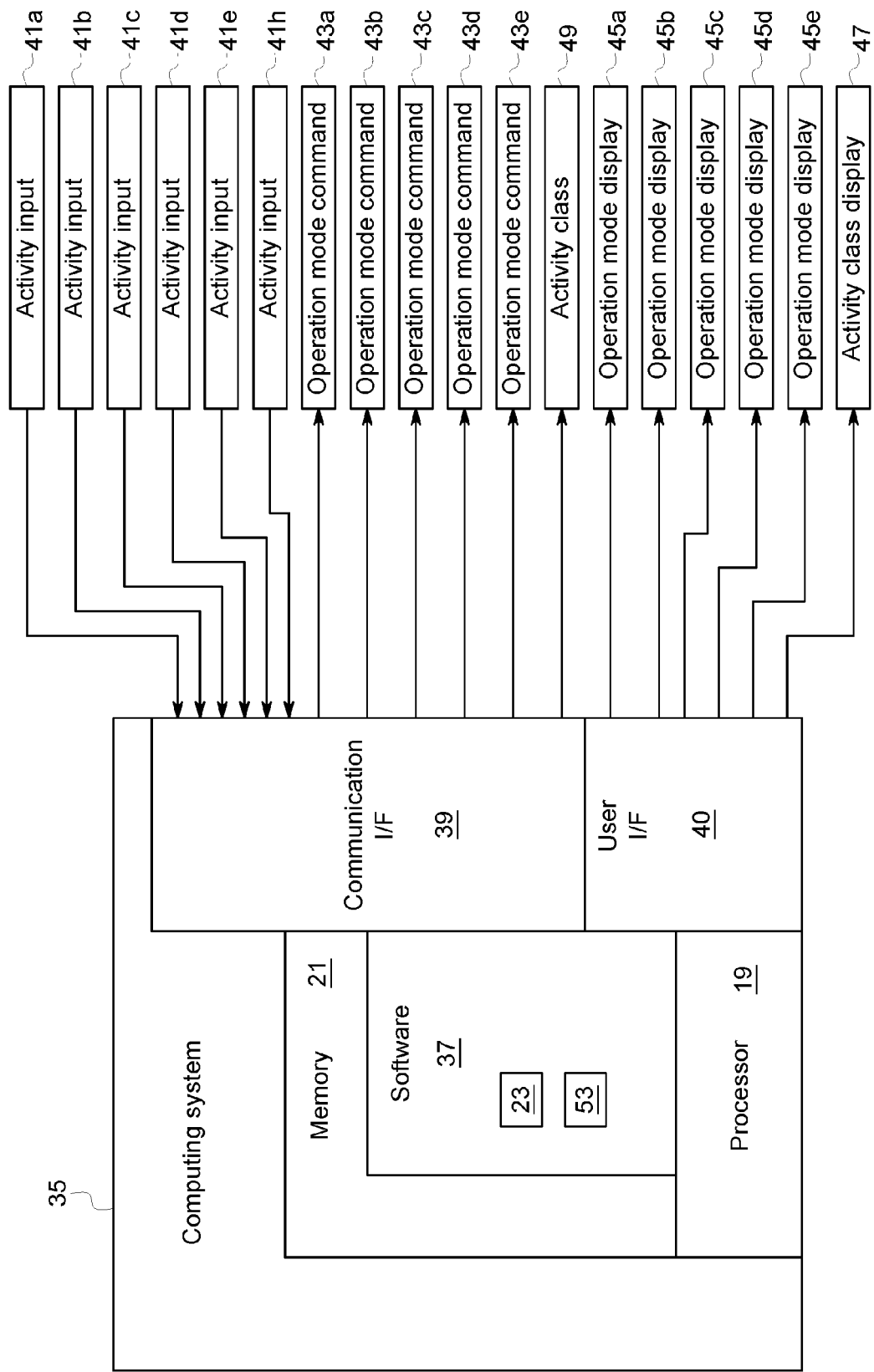
FIG. 3 is a schematic diagram of one embodiment of a computing system portion of a wireless patient monitoring system.
Figure 4:
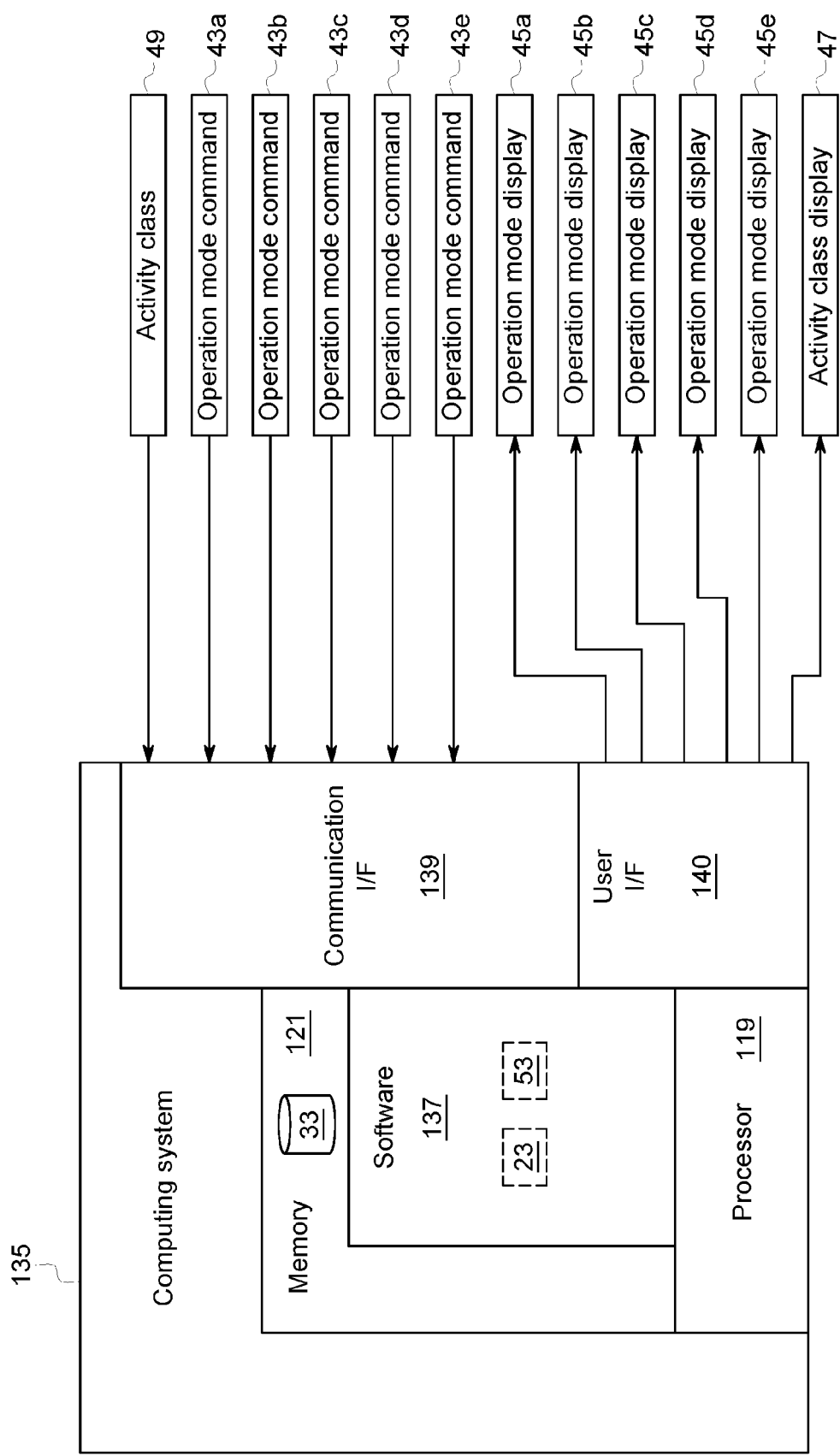
FIG. 4 is a schematic diagram of another embodiment of a computing system portion of a wireless patient monitoring system.

The hub device 15 may further include computing system 35, represented in detail in FIG. 3, having processor 19 and memory 21. The hub device 15 may serve to coordinate or control the operation mode and/or other functions of the wireless sensing devices 3a-3e, and thus may transmit operation mode commands 45a-45e to the respective wireless sensing devices 3a-3e via the communication link 11a-11e. The computing system 35 of the hub device 15 may include activity analysis module 23 that is a set of software instructions stored in memory and executable on a processor to assess the activity input(s) 41 and determine an activity class 49 therefrom. The computing system 35 of the hub device 15 may also include power management module 53 that identifies whether one or more of the wireless sensing devices 3a-3e is unreliable based on the activity class 49, and to command operation of the wireless sensing devices 3a-3e accordingly, such as to operate unreliable wireless sensing devices in a low power mode 66a or 66b. The computing system 35 of the hub device 15 may further communicate the activity class 49 and the operation mode commands 45a-45e to the computing system 135 of the host network, as illustrated in FIG. 4.

Figure 2:
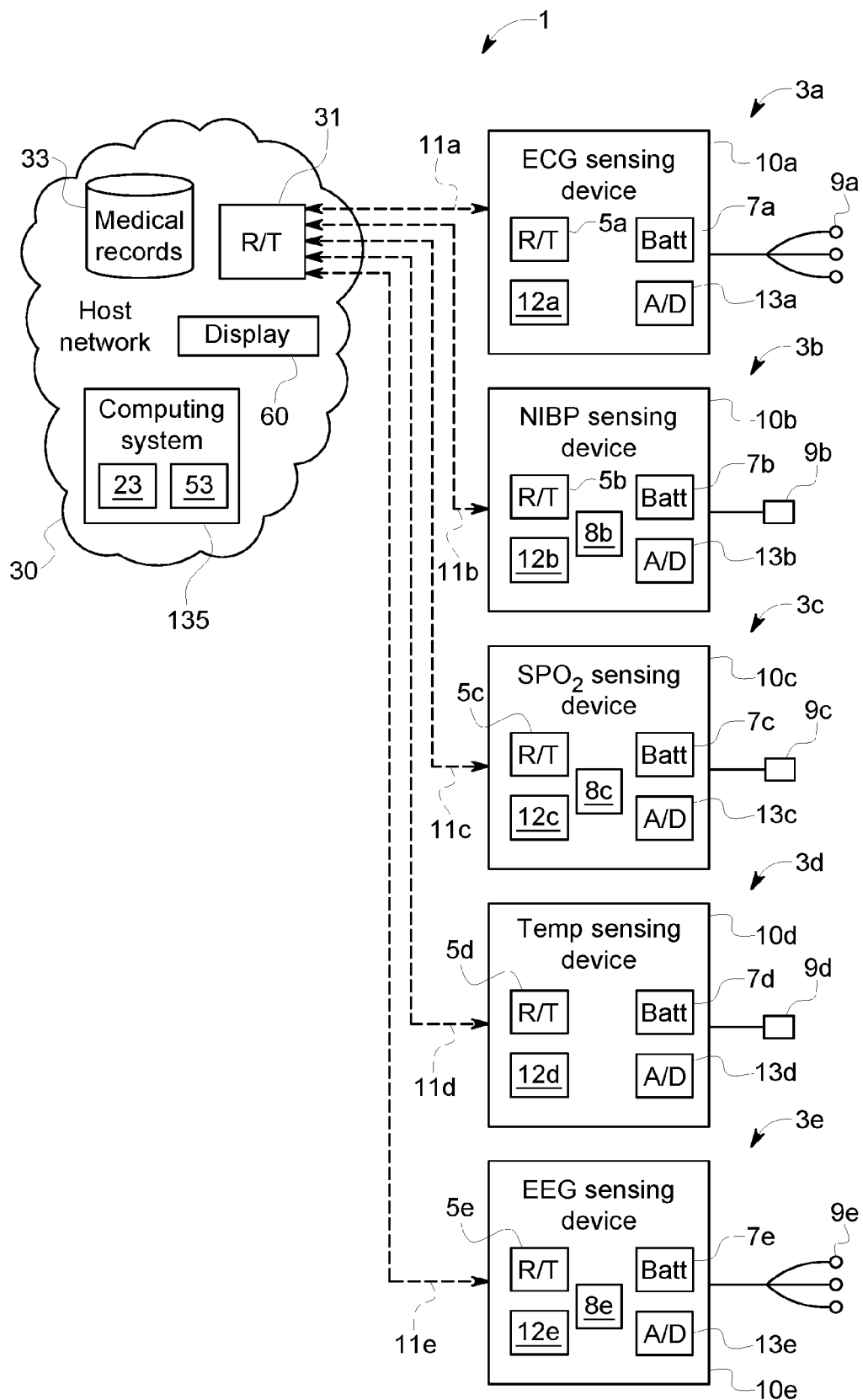
FIG. 2 is a schematic diagram of another embodiment of a wireless patient monitoring system.

In the embodiment of FIG. 2, the hub device 15 is omitted and the wireless sensing devices 3a-3e communicate directly with the host network 30, which hosts the activity analysis module 23 and the power management module 53 and generates the operation mode commands 45a-45e according to the various methods described herein. Thus, the receiver/transmitter 5a-5e of each wireless sensing device 3a-3e may communicate with a receiver/transmitter 31 associated with the host network 30 by the respective communication link 11a-11e. The communication link 11a-11e in this embodiment may operate according to any wireless communication protocol listed herein. It may be desirable to operate the communication according to a wireless communication protocol that is appropriate for longer-range transmission. For example, the wireless sensing devices 3a-3e may communicate with the host network 30 on the WMTS spectrum or on the Wi-Fi spectrum. In such an embodiment, receiver/transmitters 31 may be provided throughout a patient care facility, such as a hospital, as needed based on the system configuration and the location of patients being monitored by wireless sensor devices.

The system 1 may be configured in various embodiments such that the activity analysis module 23 and the power management module 53 is stored in memory 21 of the hub device 15 (e.g., FIG. 1). In an alternative embodiment, such as the embodiment of FIG. 2 where a hub device 15 is not present, the activity analysis module 23 and the power management module 53 may be stored in memory 121 of the computing system 135 (e.g. FIGS. 2 and 4) of the host network 30. Alternatively or additionally, the activity analysis module 23 and/or the power management module 53 may be stored in memory within one or more of the wireless sensing devices 3a-3e and executed by the respective processor 12a-12e therein. Furthermore, the activity analysis module 23 may be stored and executed in a different portion of the system 1 than the power management module 53.

Where the activity analysis module 23 is stored in memory 21 and executed on processor 19 of the hub device 15, the activity analysis module 23 may receive various activity inputs 41a-41e, 41h from various activity sensors 8a-8e, 8h throughout the system 1. For example, the activity analysis module 23 may process one or more activity inputs 41a-41e received from the wireless sensing devices 3a-3e that contain activity sensors 8a-8e, and may also receive activity input 41h from the activity sensor 8h in the hub device 15. The activity analysis module 23 may then calculate, or determine, an activity class 49 based on one or more of the activity inputs 41a-41e, 41h.

The activity class 49 is then used by the power management module 53 to determine an operation mode for each of the wireless sensing devices 3a-3e in the system. In the example depicted in FIGS. 1 and 3, the computing system 35 in the hub device 15 contains a power management module 53 that is executed within the hub device 15 to determine the operation mode for each of the wireless sensing devices 3a-3e based on the activity class 49, and then to transmit an operation command 43a-43e via wireless communication links 11a-11e to each of the wireless sensing devices 3a-3e.

Further, the hub device 15 may have a display 55 which may be controlled, such as by the processor 19, to display an operation mode display(s) 45a-45e that displays the operation mode for one or more of the wireless sensing devices 3a-3e within the system 1. For example, the operation mode display(s) 45a-45e may represent the respective operation modes in graphical form or text form on the display 55 of the hub device 15. Further, the display 55 may be controlled to display the activity class display 47, which represents the activity class 49. For example, the activity class display 47 may represent the activity class 49 in graphical form or text form, which is exemplified and discussed with respect to FIG. 6.

Figure 6:
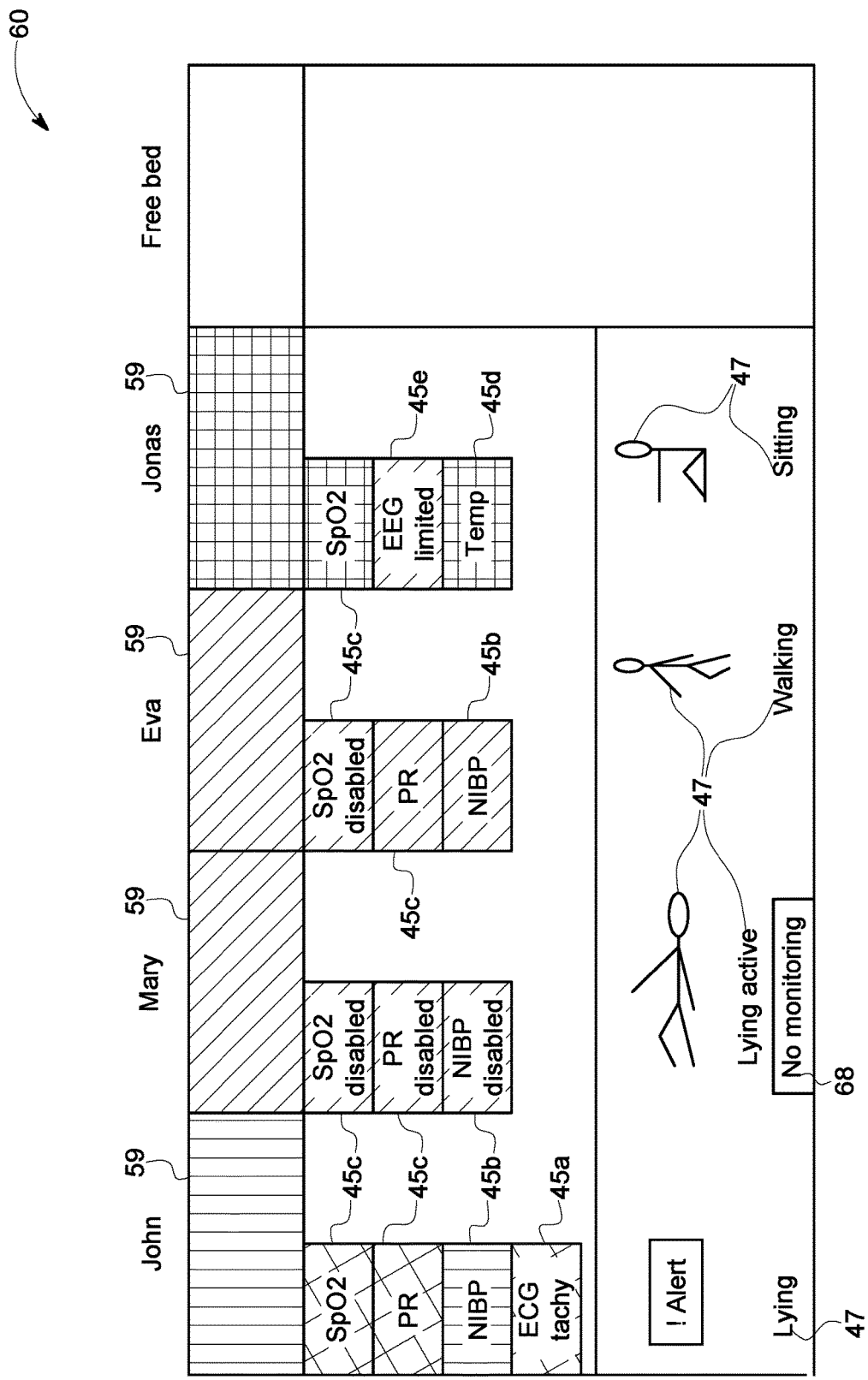
FIG. 6 depicts one embodiment of a central patient monitoring display.

Alternatively or additionally, the hub device 15 may transmit the operation mode commands 43a-43e and/or the activity class 49 to the host network 30. In such an embodiment, computing system 135 within the host network 30 may receive the operation mode commands 43a-43e and/or the activity class 49 and may operate a display 60 to display the operation mode displays 45a-45e and/or the activity class display 47, which is exemplified in FIG. 6 showing an exemplary central patient monitoring display 60.

In another embodiment of the system 1 having a hub device 15, the computing system 135 within the host network 30 may contain the activity analysis module 23 and/or the power management module 53. Thus, in various embodiments, the computing system 35 within the hub device 15 may perform a portion of the processing steps, and other processing steps may be performed by the computing system 135 within the host network 30. For example, the activity analysis module 23 may be stored and executed within the computing system 35 of the hub device 15, and the power management module 53 may be stored and executed by the computing system 135 within the host network 30, such as in order to reduce the processing load and battery consumption of the hub device 15. The allocation and execution of these operations may be controlled, for example, based on the charge status of the battery 7h in the hub device 15 or based on the available processing bandwidth of the hub device 15.

In still other embodiments, each wireless sensing device 3a-3e may contain a power management module 53 stored in memory and executed on each respective processor 12a-12e. Each wireless sensor may then receive the activity class 49 from the hub device 15, and may determine the operation mode for itself based on the activity class 49. In still other embodiments, each wireless sensing device 3a-3e may have its own activity analysis module 23 and/or power management module 53, and thus may determine the activity class based on locally-received activity input 41 and/or assign an operation mode accordingly. In some embodiments, this local determination may be supplemented by, modified by, or overridden by parallel analysis conducted at the hub device 15 and transmitted to the respective wireless sensing device 3a-3e.

The hub device 15 may communicate with host network 30 via a wireless communication link 28, such as to transmit the parameter datasets for the respective wireless sensing devices 3a-3e for storage in the patient's medical record. The hub device 15 has receiver/transmitter 25 that communicates with a receiver/transmitter 31 associated with the host network 30 on communication link 28, which may operate according to a network protocol appropriate for longer-range wireless transmissions, such as on the wireless medical telemetry service (WMTS) spectrum or on a Wi-Fi-compliant wireless local area network (LAN). The host network 30 may be, for example, a local computer network having servers housed within a medical facility treating the patient, or it may be a cloud-based system hosted by a cloud computing provider. The host network 30 may include a medical records database 33 housing the medical records for the patient, which may be updated to store the parameter datasets recorded and transmitted by the various wireless sensing devices 3a-3e. The host network 30 may further include other patient care databases, such as for monitoring, assessing, and storing particular patient monitoring data. For example, the host network may include an ECG database, such as the MUSE ECG management system produced by General Electric Company of Schenectady, N.Y.

In various embodiments, the hub device 15 may contain software for processing the physiological signals recorded by the various wireless sensing devices 3a-3e. For example, in one embodiment the individual wireless sensing device(s) 3a-3e may perform minimal or no signal processing on the physiological data measured from the patient, and may simply transmit the digitized physiological data recorded from the respective sensors 9a-9e along with the activity input 41a-41e from the activity sensors 8a-8e therein. Software stored in the hub device 15 may then be executed on the processor 19 to calculate various useful parameters from the physiological data. In still other embodiments, minimal or no signal processing may be performed in the hub device 15, and the hub device 15 may simply serve to relay the parameter datasets and activity inputs 41a-41e from the wireless sensing devices 3a-3e (an activity input 41h from activity sensor 8h, if present) to the host network 30. In such an embodiment, the activity analysis module 23 and the power management module 53 may reside in the computing system 135 of the host network 30 (as depicted in dashed lines in FIG. 4).

FIG. 3 provides a system diagram of an exemplary embodiment of the computing system 35 having an activity analysis module 23 and a power management module 53 executable to control the operation modes of the wireless sensing devices 3a-3e. The computing system 35 includes a processor 19, memory 21, software 37, and communication interface 39. The processor 19 loads and executes software 37 from memory 21, including the activity analysis module 23 and a power management module 53, which is an application within the software 37. Each of the activity analysis module 23 and a power management module 53 include computer-readable instructions that, when executed by the computing system 35 (including the processor 19), direct the operation as described in detail herein, including to calculate the patient condition index and assign the measurement intervals for the wireless sensing devices 3a-3e.

Although the computing system 35 as depicted in FIG. 3 includes one software element 37 encapsulating one activity analysis module 23 and one power management module 53, it should be understood that one or more software elements having one or more modules may provide the same operation. Similarly, while the description provided herein refers to a single computing system 35 having a single processor 19, it is to be recognized that implementations of such systems can be performed using one or more processors, which may be communicatively connected, and such implementations are considered to be within the scope of the description. Likewise, the computing system 35 may be implemented as several computing systems networked together, including in a cloud computing environment. Such an embodiment may be utilized, for example, where the computing system 35 is part of the host network 30.

The same is also true for the exemplary computing system 135 in the host network 30, which in the depicted embodiment receives the activity class 49 and the operations mode commands 43a-43e from the hub device 15 and operates the central patient monitoring display 60 to display the operation mode displays 45a-45e and the activity class display 49.

For each of the computing systems 35 and 135, memory 21 and 121 (which in some embodiments of the computing system 135 may include the medical record database 33) can comprise any storage media, or group of storage media, readable by processor 19, 119 and/or capable of storing software 37, 137. The memory 21, 121 can include volatile and non-volatile, removable and non-removable storage media implemented in any method or technology for storage of information, such as computer-readable instructions, data structures, program modules, or other data. Memory 21, 121 can be implemented as a single storage device but may also be implemented across multiple storage devices or subsystems. For example, in computing system 135 the software 137 may be stored on a separate storage device than the medical record database 33. Further, in some embodiments the memory 121 may also store the medical record database 33, which could also be distributed, and/or implemented across one or more storage media or group of storage medias accessible within the host network 30. Similarly, medical record database 33 may encompass multiple different sub-databases at different storage locations and/or containing different information which may be stored in different formats.

Examples of memory devices, or storage media, include random access memory, read only memory, magnetic discs, optical discs, flash memory, virtual memory, and non-virtual memory, magnetic sets, magnetic tape, magnetic disc storage or other magnetic storage devices, or any other medium which can be used to storage the desired information and that may be accessed by an instruction execution system, as well as any combination or variation thereof, or any other type of storage medium. Likewise, the storage media may be housed locally with the processor 19, or may be distributed in one or more servers, which may be at multiple locations and networked, such as in cloud computing applications and systems. In some implementations, the store media can be a non-transitory storage media. In some implementations, at least a portion of the storage media may be transitory. Memory 21, 121 may further include additional elements, such a controller capable, of communicating with the processor 19, 119.

The communication interface 39 of computing system 35 is configured to provide communication between the processor 19 and the various other devices within the system 1, including the wireless sensing devices 3a-3e to receive the activity inputs 41a-41e and the physiological data from each respective wireless sensing device 3a-3e, and to transmit the operation mode command 43a-43e and/or activity class 49 to each respective device 3a-3e. For example, the communication interface 39 may include the receiver/transmitters 17 and 25 described above with respect to the embodiment of FIG. 1. The communication interface 139 of computing system 135 is configured to provide communication between the processor 119 and the relevant other devices within the system 1, including the hub device 15 to receive the activity class 49 and/or operation mode commands 43a-43e. In embodiments where the wireless sensing devices 3a-3e communicate directly with the host network 30, the communication interface 139 may facilitate such communication. For example, the communication interface 139 may include the receiver/transmitters receiver/transmitter 31 described above with respect to the various embodiments of FIGS. 1 and 2.

FIG. 6 depicts an exemplary display on a central patient monitoring display 60, such as may be provided at a nurse's station on a floor of the health care facility. The exemplary central patient monitoring display 60 presents a monitoring summary from four patients being monitored by patient monitoring systems 1. The top colored block is an overall patient status display 59 representing the patient's overall status as a color, such as red for a patient experiencing an alarm condition, yellow for a patient presenting abnormalities in the recorded physiological data, and green for a patient for which all monitors indicate a normal condition.

Underneath the overall patient status display 59 is an operation mode display 45 for each physiological parameter being recorded by a wireless sensing device 3a-3e. Specifically, where an ECG sensing device 3a is implemented in the relevant monitoring system 1 on the patient, an operation mode display 45a is presented for each physiological parameter being recorded. Where an NIBP sensing device 3b is in use on a patient, the operation mode display 45b is presented for that patient. Where an SpO2 sensing device 3c is in use on a patient, an operation mode display 45c is presented for that patient. Where a temperature sensing device 3d is in use on a patient, an operation mode display 45d is presented for that patient. Where an EEG sensing device 3e is in use monitoring the patient, operation mode display 45e is presented for that patient. Various graphical display elements and methods may be used for the operation mode displays 45a-45e. In the depicted embodiment, the operation mode displays 45a-45e include a box listing the respective wireless sensing device 3a-3e and/or recorded physiological parameter. In the depicted embodiment, the operation mode display 45a-45e includes the word "disabled" if the respective wireless sensing device 3a-3e is in a low power mode where the device is disabled (such as the low power mode B 66b shown and described with respect to FIG. 5). The exemplary operation mode display 45a-45e includes the word "limited" if the respective wireless sensing device 3a-3e is being operated in a low power mode where a limited monitoring function is being employed (such as low power mode A 66a shown and described with respect to FIG. 5). In the example, the operation mode display 45a-45e are plain without any text to indicate that the respective wireless sensing device 3a-3e is operating in a standard operating mode 64. Additionally, the same display area may be used to indicate the status of the physiological data recorded from that respective wireless sensing device 3a-3e, such as by providing a red, yellow, or green color as described above with respect to the overall patient status display 59.

In addition to the operation mode displays 45a-45e for each patient, an activity class display 47 may show the activity class 49 for the respective patient. In the depicted embodiment, the activity class displays 47 depict the activity class 49 in word form, and some also include a graphic representing the activity class 49. In situations where all of the wireless sensing devices 3a-3e monitoring a patient are operating in a low power mode, such as being "disabled", an additional "no monitoring" warning display 68 may be provided to advise clinicians that the patient is not currently being monitored due to their activity level.

Figure 7:
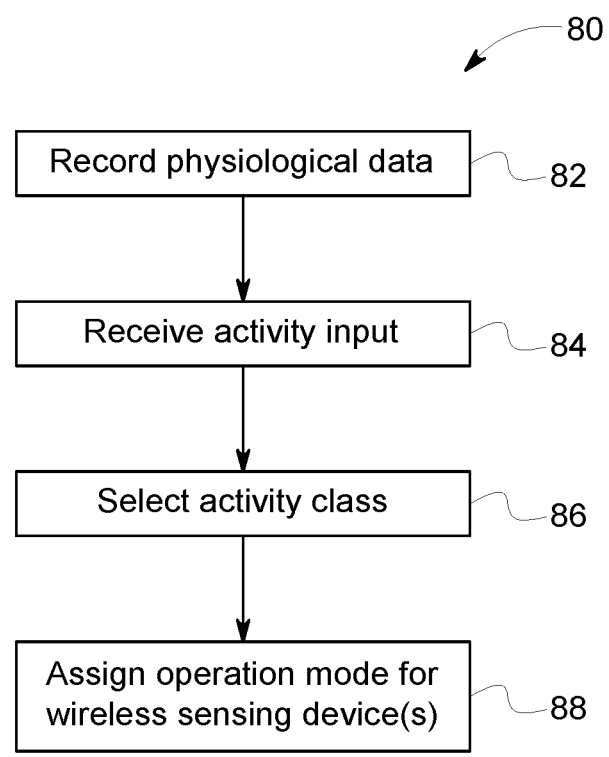
FIG. 7 is a flow chart depicting one embodiment of a method of monitoring a patient.

FIG. 7 depicts one embodiment of a method 80 of monitoring a patient. At step 82, physiological data is recorded using one or more wireless sensing devices 3a-3e within the patient monitoring system 1. At step 84, activity input is received, such as at processor 12, 19, 119, that will execute the activity analysis module 23. An activity class is selected at step 86, such as by executing the activity analysis module 23 on the respective processor 12, 19, 119. An operation mode 64, 66a, 66b is assigned for one or more of the wireless sensing devices within the patient monitoring system 1 at step 88.

Figure 8:
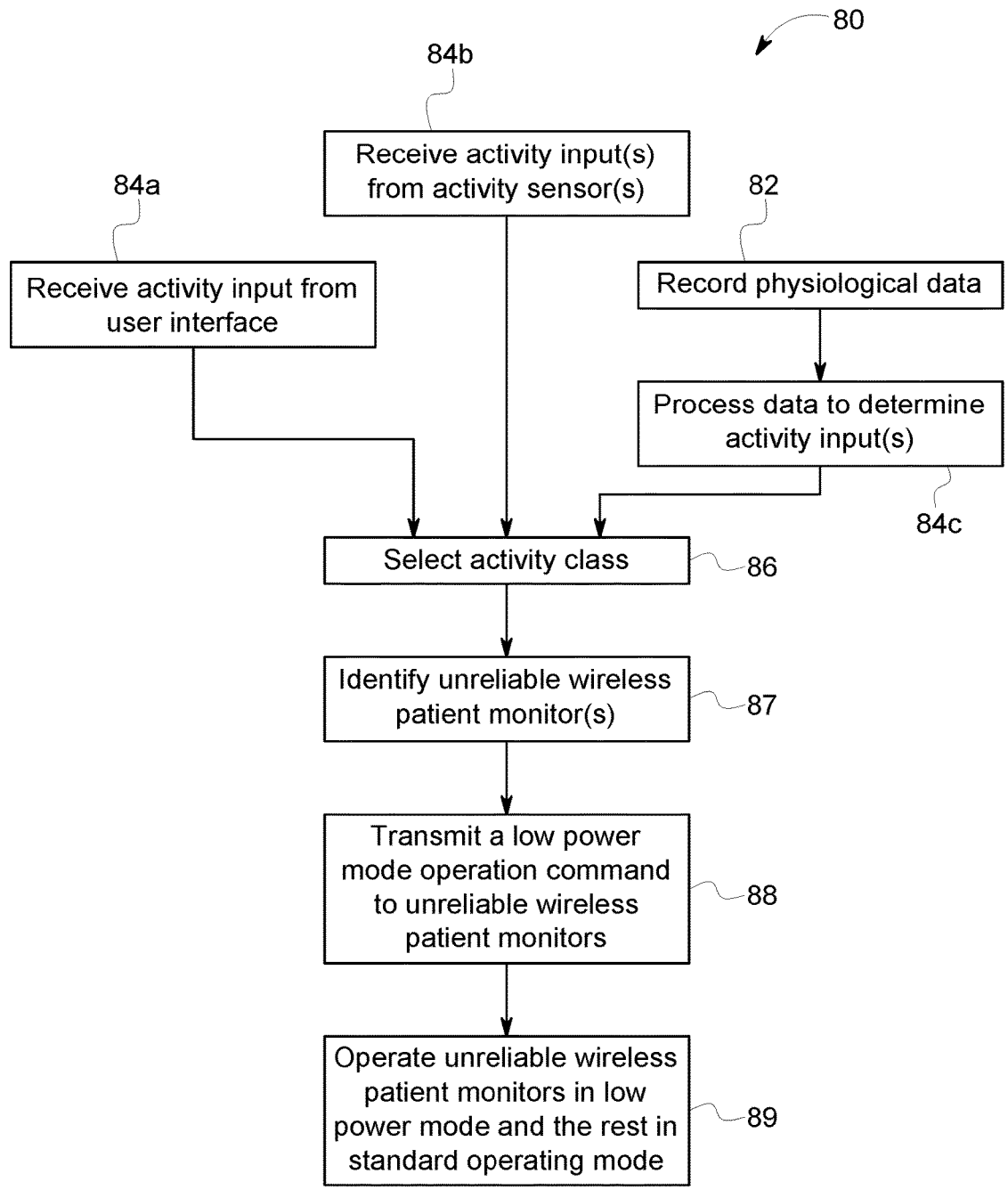
FIG. 8 is a flow chart depicting another embodiment of a method of monitoring a patient.

FIG. 8 depicts another embodiment of a method 80 of monitoring a patient. Physiological data is recorded at step 82, and activity input 41a-41e, 41h is received at steps 84a, 84b, and 84c. Specifically, the physiological data is processed at step 84c to determine activity inputs 41a-41e, which may be executed by the processors 12a-12e of one or more of the wireless sensing devices 3a-3e, the processor 19 of the computing system 35 in the hub device 15, or the processor 119 of the computing system 135 in the host network 30. Likewise, the activity inputs received at steps 84a and 84b may be received at any of those processors as well. At step 84a, the activity input 41h received from a user interface may be, for example, from the mode input button 57 at the hub device 15. The activity inputs 41a-41e, 41h received from activity sensors at step 84b may be from one or more sensors 8a-8e and 8h distributed throughout the patient monitoring system 1 as described above. In various embodiments, only a subset of these activity inputs 41a-41e, 41h may be received. An activity class 49 is selected based on the activity inputs 41a-41e, 41h at step 86. Unreliable wireless sensing devices are identified at step 87 based on the activity class 49. A low power mode operation mode command 43a-43e is transmitted to those unreliable wireless sensing devices at step 88. At step 89, the unreliable wireless sensing devices are operated in low power mode 66a, 66b and the rest of the wireless sensing devices are operated in standard operating mode 64. Each of the wireless sensing devices 3a-3e is continually operated based on the activity input(s) 41a-41e, 41h, and the unreliable wireless sensing devices will be returned to standard operating mode 64 once the relevant activity input(s) 41a-41e, 41h and/or the activity class 49 indicates that the physiological data gathered therefrom will be reliable. In various embodiments, the activity input(s) 41a-41e, 41h may be received and continuously or periodically, such as by the computing system 35, 135 or processor 12a-12e (depending on the configuration of the system 1, as described above).

This written description uses examples to disclose the invention, including the best mode, and also to enable any person skilled in the art to make and use the invention. Certain terms have been used for brevity, clarity and understanding. No unnecessary limitations are to be inferred therefrom beyond the requirement of the prior art because such terms are used for descriptive purposes only and are intended to be broadly construed. The patentable scope of the invention is defined by the claims, and may include other examples that occur to those skilled in the art. Such other examples are intended to be within the scope of the claims if they have features or structural elements that do not differ from the literal language of the claims, or if they include equivalent features or structural elements with insubstantial differences from the literal languages of the claims.

I claim:

1. A patient monitoring system comprising:
   one or more wireless sensing devices, each wireless sensing device configured to record physiological data from a patient to measure a physiological parameter of the patient;
   one or more processors;
   an activity analysis module executable on one or more of the processors to select an activity class from a predefined set of activity classes based on an activity input;
   a power management module executable on one or more of the processors to reduce power consumption of the one or more of the wireless sensing devices by:
     identifying that the one or more of the wireless sensing devices is unreliable to measure the physiological parameter based on the activity class when the activity class indicates that the physiological data will be unreliable due to patient position or artifact caused by motion of the patient; and
     operating the one or more identified unreliable wireless sensing devices in a low power mode.

2. The patient monitoring system of claim 1, wherein the unreliable wireless sensing device in the low power mode does not record physiological data from the patient when the activity class indicates that the physiological data will be unreliable due to patient position or artifact caused by motion of the patient.

3. The patient monitoring system of claim 1, wherein the unreliable wireless sensing device in the low power mode records a reduced set of physiological data from the patient when the activity class indicates that the physiological data will be unreliable due to patient position or due to artifact caused by motion of the patient.

4. The patient monitoring system of claim 1, wherein the unreliable wireless sensing device in the low power mode records the physiological data from the patient less frequently when the activity class indicates that the physiological data will be unreliable due to patient position or due to artifact caused by motion of the patient.

5. The patient monitoring system of claim 1, further comprising at least one activity sensor configured to sense at least one of a position of the patient and a motion of the patient to provide the activity input, wherein the activity sensor includes at least one of an accelerometer and a gyroscope.

6. The patient monitoring system of claim 5, wherein the at least one activity sensor is in at least one of the wireless sensing devices to provide the activity input.

7. The patient monitoring system of claim 1, further comprising a hub device in wireless communication with the one or more wireless sensing devices, the hub device containing the activity analysis module, the power management module, and the processor on which the activity analysis module and the power management module are executed.

8. The patient monitoring system of claim 7, further comprising at least one activity sensor in the hub device configured to sense at least one of a position of the patient and a motion of the patient to provide the activity input.

9. The patient monitoring system of claim 8, further comprising at least one activity sensor in at least one of the wireless sensing devices configured to sense at least one of a position of the patient and a motion of the patient to provide the activity input.

10. The patient monitoring system of claim 1, wherein the activity input includes a user-provided input.

11. The patient monitoring system of claim 1, wherein the activity analysis module is further executable on the processor to detect the activity input as a feature in the physiological data recorded by the one or more wireless sensing devices.

12. The patient monitoring system of claim 1, further comprising at least a wireless non-invasive blood pressure (NIBP) device, wherein the wireless NIBP device is operated in the low power mode to stop recording a blood pressure from the patient if the activity class indicates that the patient is moving.

13. The patient monitoring system of claim 1, further comprising at least a wireless pulse oximeter device configured to record an SPO2 and a pulse rate from the patient, wherein the wireless pulse oximeter device is operated in the low power mode to stop operation of at least one of a red LED and an infrared LED if the activity class indicates that the patient is moving.

14. The patient monitoring system of claim 1, further comprising at least an wireless electrocardiograph (ECG) device, wherein the wireless ECG device is operated in the low power mode to record only a heart rate using a reduced-lead set from the patient for one or more given activity classes.

15. A method of monitoring a patient, the method comprising:
    recording physiological data from a patient with each of at least two wireless sensing devices, wherein each wireless sensing device of the at least two wireless sensing devices measures a different type of physiological data to measure a different physiological parameter of the patient;
    receiving an activity input at a processor;
    selecting with the processor an activity class based on the activity input;
    identifying at least one wireless sensing device that is unreliable to measure the physiological parameter based on the activity class when the activity class indicates that the physiological data will be unreliable due to patient position or artifact caused by motion of the patient; and
    changing operation of the identified unreliable wireless sensing devices into a low power mode.

16. The method of claim 15, further comprising presenting on a display at least one of an operation mode display indicating that the unreliable wireless sensing devices are operating in a low power mode and an activity class display indicating the activity class.

17. The method of claim 15, further comprising recording the activity input with at least one activity sensor, wherein the activity input includes at least one of a orientation information and a motion information.

18. The method of claim 15, wherein the receiving selecting and identifying steps are carried out in a hub device in wireless communication with each of the at least two wireless sensing devices, and the operating step is carried out by the hub device wirelessly communicating an operation mode command to each wireless sensing device.

19. The method of claim 15, wherein the unreliable wireless sensing device in the low power mode does at least one of not recording physiological data from the patient, recording a reduced set of physiological data from the patient, or recording the physiological data from the patient less frequently when the activity class indicates that the physiological data will be unreliable due to patient position or artifact caused by motion of the patient.

20. The method of claim 15, wherein the activity class is selected from a predefined set of activity classes that includes one or more of a lying class, a reclining class, a sitting class, a standing class, a moving class, a walking class, and a moving hand or finger class.

21. The method of claim 15, further comprising:
    reselecting an activity class based on a new activity input;
    identifying that one or more of the unreliable sensing devices is no longer unreliable to accurately measure the physiological parameter based on the activity class; and
    changing operation of the sensing device that is no longer unreliable into a standard operating mode.

* * * * *